United States Patent [19]

Fujii

[11] Patent Number: 4,717,811
[45] Date of Patent: Jan. 5, 1988

[54] DIFFERENTIAL RESISTANCE HUMIDITY DETECTOR

[75] Inventor: Masanobu Fujii, Yao, Japan

[73] Assignee: Sharp Kabushiki Kaisha, Osaka, Japan

[21] Appl. No.: 913,251

[22] Filed: Sep. 30, 1986

[30] Foreign Application Priority Data

Sep. 30, 1985 [JP] Japan .................. 60-150666[U]

[51] Int. Cl.$^4$ ............................................. H05B 1/02
[52] U.S. Cl. ................................. 219/497; 219/501; 219/483; 219/505; 324/65 R; 324/105; 73/336.5; 73/75
[58] Field of Search ............... 219/501, 504, 505, 497, 219/499, 483; 73/336.5, 338, 73, 75; 324/65 R, 105

[56] References Cited

U.S. PATENT DOCUMENTS

| 4,080,564 | 3/1978 | Nitta et al. | 324/65 R |
| 4,270,085 | 5/1981 | Terada et al. | 324/65 R |
| 4,326,414 | 4/1982 | Terada et al. | 324/65 R |
| 4,572,900 | 2/1986 | Wohltjen | 324/65 R |
| 4,594,569 | 6/1986 | Fukushima et al. | 324/65 R |

Primary Examiner—M. H. Paschall
Attorney, Agent, or Firm—Birch, Stewart, Kolasch & Birch

[57] ABSTRACT

A humidity detector includes a first heat-sensing element for an electric signal corresponding to the temperature of steam to be detected and a second heat-sensing element for an atmosphere temperature whose vapor is to be detected or a temperature close to it. A comparator compares the electric signals from the first and second heat-sensing elements. The vapor detection characteristics may be adjusted through variation in the heating temperature of the first heat-sensing element.

6 Claims, 6 Drawing Figures

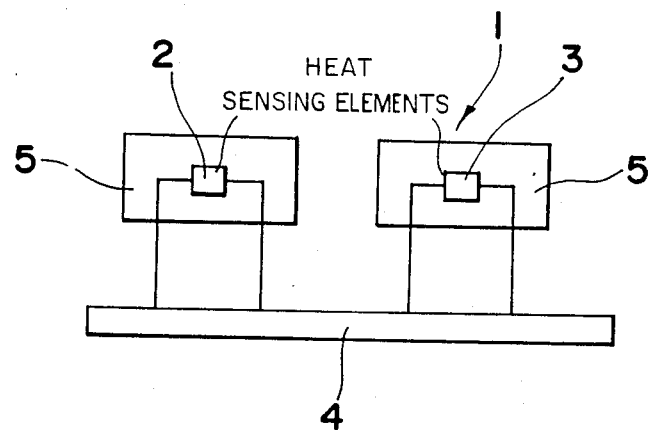
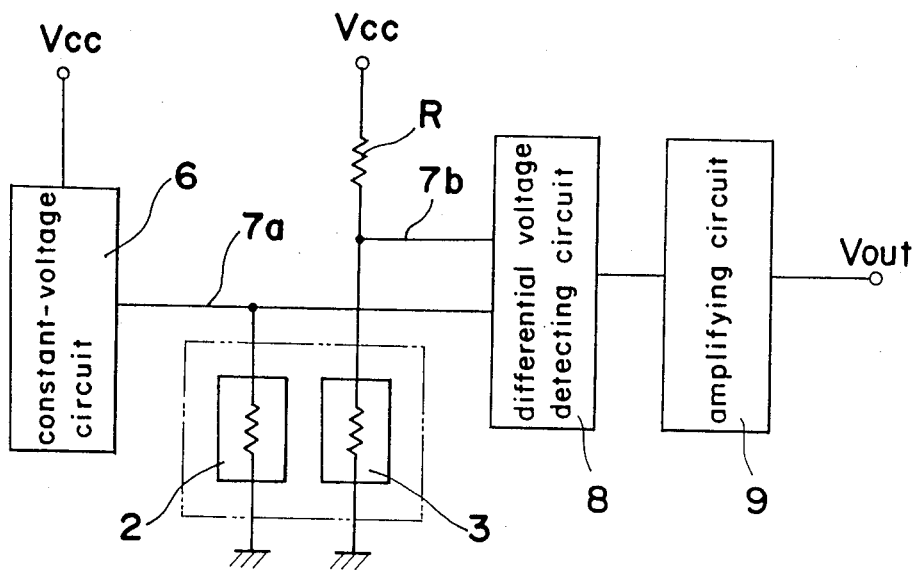
Fig. 2

DIFFERENTIAL RESISTANCE HUMIDITY DETECTOR

BACKGROUND OF THE INVENTION

1. Field of the Invention

The present invention relates to a humidity detector which is provided in, for example, a microwave oven or the like to detect, through the steam, the finished condition of the material to be cooked.

2. Description of the Prior Art

Conventionally, a humidity sensor to be used in, for example, a microwave oven, had two thermistors self-heated; one of them was sealed in dry air of 0 g per m³ in absolute humidity, the other thereof was adapted to receive the air to be discharged from within the heating chamber. However, this type of humidity sensor required two thermistors, as a pair, approximately equal in temperature coefficient and resistance value at the high temperature, thus resulting in higher cost. Also such a humidity sensor was incapable of varying the detection characteristics, so that a humidity sensor was desired which was capable of adjusting the detection characteristics for each of the microwave ovens because of variations in the volume within the electronic range, the air flow of the motor or the like.

SUMMARY OF THE INVENTION

The present invention provides a humidity detector which is capable of detecting the steam at the lower cost through the solution of the above-described technical problem, and of adjusting the detection characteristics by simple operation.

A humidity detector comprises a first heat-sensing element which guides an electric signal corresponding to the temperature, a means for heating the outer peripheral face of the first heat-sensing element to the boiling point or more of the steam to be detected, a second heat-sensing element which is adapted not to heat by itself or by a foreign means and guides an electric signal corresponding to an atmosphere temperature whose vapor is to be detected or a temperature close to it, a means for comparing the electric signals from the first and second heat-sensing elements, the vapor detection characteristics may be adjusted through variation in the heating temperature of the first heat-sensing element.

According to the present invention, when only the first heat-sensing element is heated by a heating means, the difference is caused in resistance value between it and the second heat-sensing element not heated. Accordingly, as the air containing the vapor hits against the first and second heat-sensing elements, the resistance value change correspondingly. The difference in the resistance values between the first heat-sensing element and the second heat-sensing element at this time is closely related to the heating temperature, so that the difference in the resistance values may be set through the variation in the heating temperature of the first heat-sensing element. Thus, the characteristics of the detection output value of the detector may be adjusted to the desired characteristics.

BRIEF DESCRIPTION OF THE DRAWINGS

These and other objects and features of the present invention will become apparent from the following description taken in conjunction with preferred embodiments thereof with reference to the accompanying drawings, in which:

FIG. 1 is a simplified front-face view of a humidity sensor 1 in accordance with the present invention;

FIG. 2 is an electric circuit block diagram of the humidity sensor 1;

DETAILED DESCRIPTION OF THE INVENTION

Figure 3:
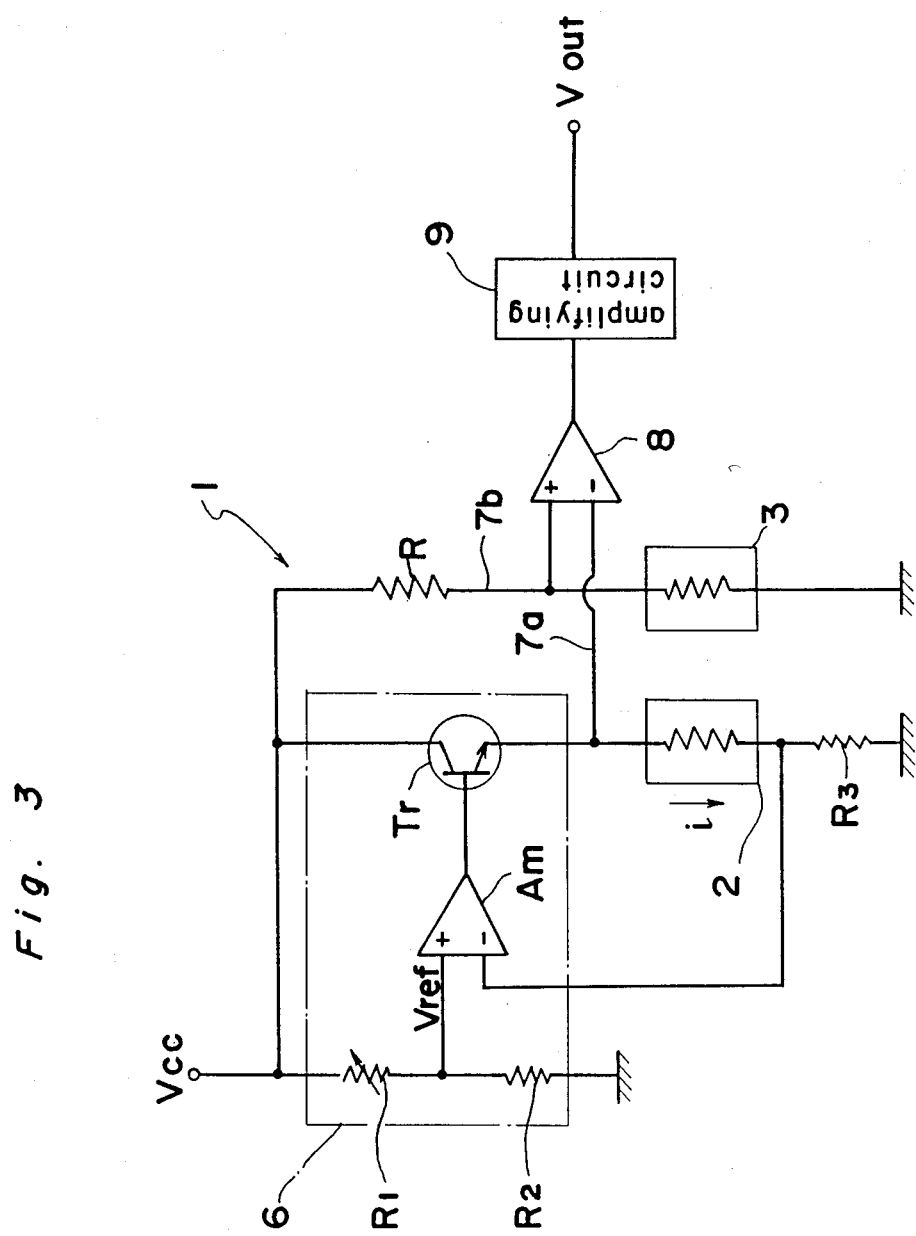
FIG. 3 is an electric circuit diagram showing examplarily the detailed arrangement of the block diagram of FIG. 2.

Referring to FIG. 1, a humidity sensor 1 includes a first heat-sensing element 2 to be heated by itself by means of the self-heating and a second heat-sensing element 3 for detecting the atmosphere temperature, the second heat-sensing element being arranged not to heat by itself or by a foreign means. Also, the first heat-sensing element may be arranged to heat by a foreign means provided in association with the first heat-sensing element. The heat-sensing elements 2 and 3 are composed of a metallic thin-film resistor, a thermistor or a semiconductor and so on. Each of the heat-sensing elements 2 and 3 is sealed individually by a metallic pipe 5 and is electrically connected by a base plate 4, respectively. The humidity sensor 1 may include, what is called, a steam detector.

Referring to FIG. 2, in an electric circuit of the humidity sensor 1, a means of power-supply voltage Vcc applied to a constant-voltage circuit 6 is connected to one input terminal of a differential voltage detecting circuit 8 through a line 7a. One terminal of the first heat-sensing element 2 is connected to the line 7a. The other terminal of the first heat-sensing element 2 is grounded. The power-support voltage Vcc is, also, applied upon the other heat-sensing element 3 through a resistor R. The power-supply voltage Vcc is divided in voltage by the resistor R and the second heat-sensing element 3, and the divided voltage is applied upon the other input terminal of the differential voltage detecting circuit 8 through a line 7b. In the differential voltage detecting circuit 8, the input voltage difference between the inputs from the lines 7a and 7b is detected and is applied to an amplifying circuit 9. The amplifying circuit 9 amplifies the input from the differential voltage detecting circuit 8 to output it as the sensor output of the humidity sensor 1.

Referring to FIG. 3, for instance, the constant voltage circuit 6 consists of a pair of resistors R1 and R2 connected to the Vcc, a transistor Tr connected to the first heat-sensing element 2, and an operational amplifier Am connected between the base of the transistor and the connecting point between the pair of resistors. Also, the differential voltage detecting circuit 8 consists of an operatonal amplifier of which two input terminals are connected with the first heat-sensing element 2 and second heat-snsing element 3, respectively. With the arrangement of FIG. 3, the electric current i flowing in the first heat-sensing element 2 may be represented by an equation of $i = V_{ref}/RS$, and the electric current i has a relationship with the heating temperature T of the first heat-sensing element 3 as represented by an equation $T \propto i$. Accordingly, to control the temperature of the first heat-sensing element 3, it needs enough to control the i which depends on either the variation of the $V_{ref}$ or the variation of the RS. Upon controlling the electric current i to be flow in the first heat-sensing element 2, the operational characteristics of the humidity sensor 1 can be varied. To change the $V_{ref}$, the resistor R1 consists of a variable resistor of which resistance can be changed. In addition, the value of the V1 may be changed to vary the $V_{ref}$. The output $V_{out}$ of the amplifying circuit shows an output of the humidity sensor 1 having a specific value of characteristics, which is a signal amplifying the difference of the voltage variation against steam to be detected between the pair of heat-sensing elements 2 and 3.

Figure 4:
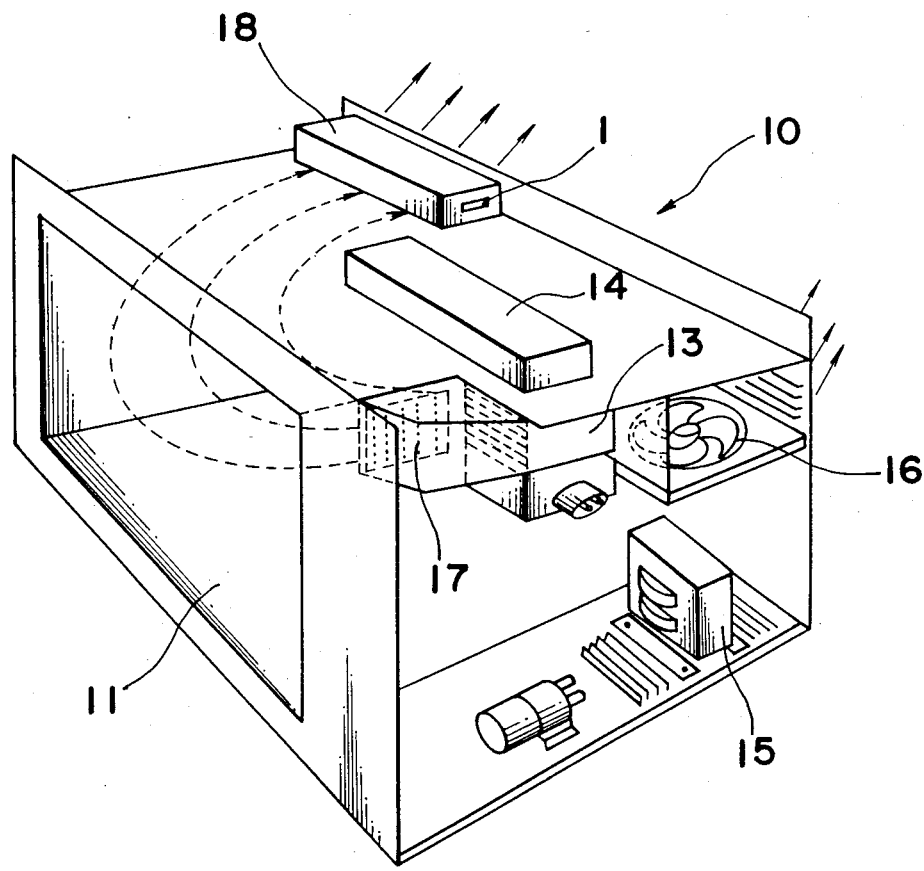
FIG. 4 is a perspective view of an electronic range 10 using the humidity sensor 1.

FIG. 4 is a perspective view of an electronic range 10 which has the humidity sensor 1. The electromagnetic waves from a magnetron 13 are fed through a waveguide 14 into a cooking chamber 11 of the electronic range 10. The magnetron 13 and a high-tension transformer 15 are cooled by a cooling fan 16. Also, the radiation of magnetron 13 together with warm air which is caused by the material to be cooked within the cooking chamber 11 through ventilation holes 17 provided on the chamber walls of the cooking chamber 11, is discharged to the exhaust duct 18. The humidity sensor 1 in accordance with the present invention is provided in this exhaust duct 18. The steam caused by the heating of the material to be cooked within the electronic range 10 as described is detected by the humidity sensor 1 provided within the exhaust duct 18, when it is discharged into the exhaust duct 18, in order to check the finished condition of the material to be cooked.

The principle according to which the steam amount is detected by the humidity sensor 1 will be described in detail hereinafter. The basic principle is the same as a hot-wire type current meter, the energy preservation rule of the following equation (1) is formulated in the thermal balance condition where the heating temperature of the first heat-sensing element 2 remains unchanged.

$$\frac{dqg}{dt} dv = \frac{dqt}{dt} ds \qquad (1)$$

qg: heating value per unit volume
qt: cooling heat transfer amount per unit area The left-hand side of equation (1) shows the thermal amount per unit area to be cause per unit time by the first heat-sensing element 2, the right-hand side shows the total thermal transfer amount to be transmitted to the exhaust air from the surface of the first heat-sensing element 2. Fourier's law and Ohm's law, which are well known in heat transfer engineering, are applied to equation (1).

$$\rho \cdot J^2 dv = h \cdot (T\omega - Tf) ds \qquad (2)$$

$\rho$: electric resistivity of the second heat-sensing element 3
J: electric current density
h: local heat-transfer coefficient
$T\omega$: wall-face temperature of the second heat-sensing element 3
Tf: temperature of air to be exhausted from within the heating chamber The integral of equation (2) is $$RH \cdot I^2 = hm \cdot (T\omega - Tf) \cdot S \qquad (3)$$

RH: electric resistance of the second heat-sensing element 3
I: electric current flowing through the second heat-sensing element 3
hm: average heat transfer coefficient
S: surface area of the second heat-sensing element 3

The average heat-transfer coefficient depends upon the average wind speed of the exhaust air and also depends even upon the steam amount contained in the exhaust wind. As the average wind speed is determined unconditionally when the exhaust system of the electronic range is decided, the average heat-transfer coefficient changes by the steam amount contained by the exhaust wind. When the $T\omega$ is constant, the Tf is measured by the second heat sensing element 3, also when the resistance value RH or the current value I of the first heat-sensing element 2 is measured, the hm is provided, so that the steam amount to be contained in the exhaust wind is provided.

Figure 5:
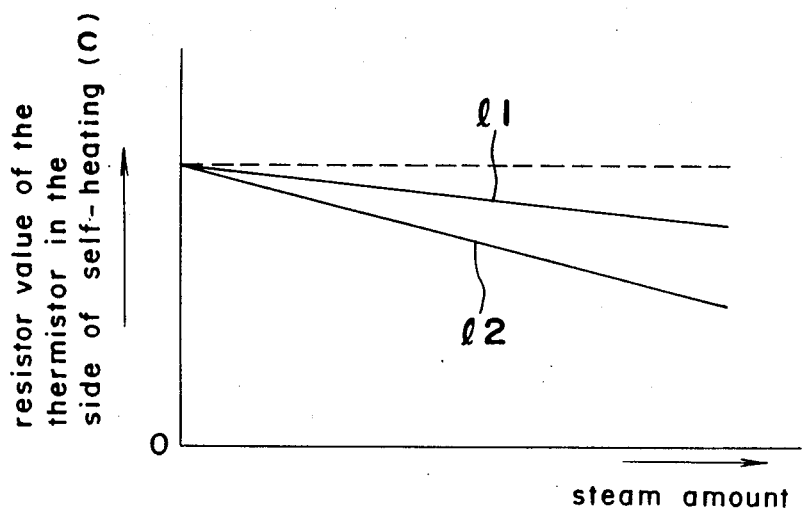
FIG. 5 is a graph showing the relationship between the steam amount of the first heat-sensing element 2 on the side of the self-heating and the resistance value.

FIG. 5 is a graph showing the variation in the resistance value in response to the steam amount when the heating temperature of the first heat-sensing element 2 is changed in various ranges. In FIG. 5, reference character 11 shows a case where the current value is small, i.e., a case where the heating temperature is low and reference character 12 shows a case where the current is large, i.e., where the heating temperature is high. As apparent from FIG. 5, increase the heating temperature with the current value flowing to the heat-sensing element 2 being large, and the variation amount of the resistance value of the first heat-sensing element 2 with respect to the steam amount increases.

Figure 6:
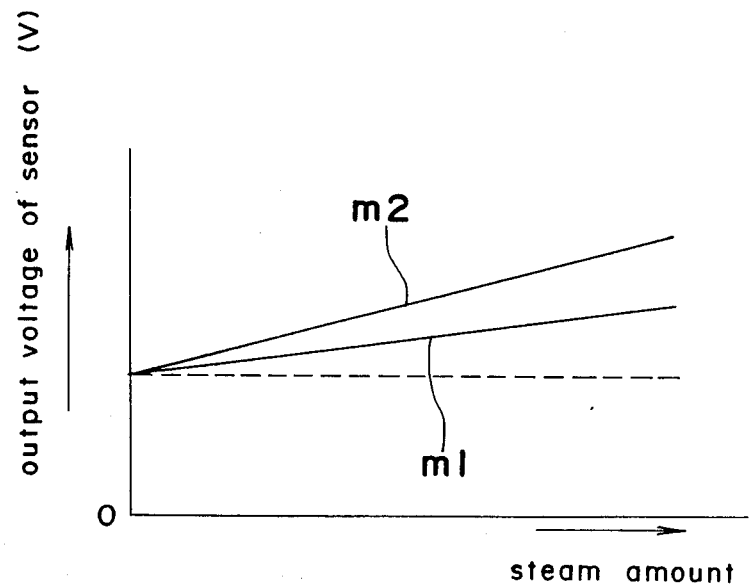
FIG. 6 is a graph showing the relationship between the steam amount of the humidity sensor 1 and the humidity sensor output voltage value.

The relationship between the output voltage value of the humidity sensor 1 and the steam amount at this time is shown in FIG. 6. Reference character m1 corresponds to reference character 11 of FIG. 5 and reference character m2 corresponds to reference character 12 of FIG. 5. As is apparent from FIG. 5, the variation in the output voltage value from the humidity sensor 1 increases as the difference in the resistance value between the first heat-sensing element 2 and the second heat-sensing element 3 is larger. Accordingly, the sensitivity with respect to the steam of the humidity sensor 1 may be varied by the magnitude of the self-heating temperature of the first heat-sensing element 2, so that the characteristics corresponding to the use of the temperature sensor 1 may be optionally selected. According to the present invention as described hereinabove, the detection characteristics of the steam detector may be simply varied through the variation in the heating temperature of the first heat-sensing element 2.

Although the present invention has been fully described by way of example with reference to the accompanying drawings, it is to be noted here that various changes and modifications will be apparent to those skilled in the art. Therefore, unless otherwise such changes and modifications depart from the scope of the present invention, they should be construed as being included therein.

What is claimed is:
1. A humidity sensor comprising:
a first heat sensing element having a first resistance;

means for heating said first heat sensing element above the boiling point of steam to be detected;

a second heat-sensing element having a second resistance;

said first and second heat sensing elements having first and second resistances which vary with respect to humidity at different rates;

differential detecting means for monitoring the difference between said first and second resistances of said first and second heating elements and developing a difference signal in response thereto, said difference signal being representative of sensed humidity.

2. The humidity sensor of claim 1 wherein a first voltage across said first heat sensing element varies in proportion to variations in the value of said first resistance and a second voltage across said second heat sensing element varies in proportion to variations in the value of said second resistance;

said differential detection means comparing said first and second voltages to develop said difference signal.

3. The sensor of claim 1 wherein said means for heating varies the amount of heat supplied said first heat sensing element to vary the detecting properties of said sensor.

4. A humidity sensor for sensing the humidity of an oven cavity comprising:

a first heat sensing element having a first resistance;

means for heating said first heat sensing element above the boiling point of steam to be detected;

a second heat sensing element having a second resistance;

said first and second heat sensing elements having first and second resistances which vary with respect to humidity at different rates, said first and second heat sensing elements being provided in an airflow exhausted from the oven cavity;

differential detecting means for monitoring the difference between said first and second resistances of said first and second heating elements and developing a difference signal in response thereto, said difference signal being representative of sensed humidity of the oven cavity.

5. The humidity sensor of claim 4 wherein a first voltage across said first heat sensing element varies in proportion to variations in the value of said first resistance and a second voltage across said second heat sensing element varies in proportion to variations in the value of said second resistance;

said differential detection means comparing said first and second voltages to develop said difference signal.

6. The sensor of claim 4 wherein said means for heating varies the amount of heat supplied said first heat sensing element to vary the detecting properties of said sensor.

* * * * *